(12) United States Patent
Rosenberg et al.

(10) Patent No.: US 10,869,748 B2
(45) Date of Patent: Dec. 22, 2020

(54) ACTIVE MONITORING PRESSURE SENSITIVE VASCULAR GRAFT

(71) Applicant: Regents of the University of Minnesota, Minneapolis, MN (US)

(72) Inventors: Michael Rosenberg, Eagan, MN (US); Sean Lester Moen, Saint Paul, MN (US); Jafar Golzarian, Plymouth, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 49 days.

(21) Appl. No.: 15/585,869

(22) Filed: May 3, 2017

(65) Prior Publication Data

US 2017/0319326 A1 Nov. 9, 2017

Related U.S. Application Data

(60) Provisional application No. 62/330,969, filed on May 3, 2016, provisional application No. 62/335,874, filed on May 13, 2016.

(51) Int. Cl.
*A61F 2/07* (2013.01)
*A61B 5/0215* (2006.01)
(Continued)

(52) U.S. Cl.
CPC ............. *A61F 2/07* (2013.01); *A61B 5/0215* (2013.01); *A61B 5/6862* (2013.01); *A61B 5/0031* (2013.01); *A61B 5/02158* (2013.01); *A61B 2560/0247* (2013.01); *A61B 2560/0462* (2013.01); *A61B 2562/0247* (2013.01); *A61B 2562/12* (2013.01); *A61B 2562/18* (2013.01);

*A61F 2/82* (2013.01); *A61F 2002/072* (2013.01); *A61F 2002/8486* (2013.01);
(Continued)

(58) Field of Classification Search
CPC .................................................. A61B 5/02158
See application file for complete search history.

(56) References Cited

U.S. PATENT DOCUMENTS

| | | | | |
|---|---|---|---|---|
| 5,151,105 A | * | 9/1992 | Kwan-Gett | ............... A61F 2/06 604/103.05 |
| 5,549,663 A | * | 8/1996 | Cottone, Jr. | ............... A61F 2/07 606/195 |

(Continued)

FOREIGN PATENT DOCUMENTS

WO    WO 02/098296 A1    12/2002

OTHER PUBLICATIONS

Santos, *Improving Post-EVAR Surveillance with a Smart Stent-Graft*, Technologies for medical sciences, Book Series: Lecture Notes in Computational Vision and Biomechanics, Chapter 14, vol. 1 (Natal Jorge, R.M.; Tavares, J.M.R.S.; Pinotti Barbosa, M.; Slade, A.P., Eds.) (2012).

*Primary Examiner* — Jacqueline Woznicki

(74) *Attorney, Agent, or Firm* — Patterson Thuente Pedersen, P.A.

(57) ABSTRACT

A vascular graft includes deformable sleeves that include an electrical component. The electrical component can be variable-resistance or piezoelectric, in embodiments, such that deformation of the sleeves due to pressure changes create or modify an electrical signal. A transponder can then transmit information relating to the pressure inside and outside of the vascular graft.

12 Claims, 8 Drawing Sheets

(51) Int. Cl.
  *A61B 5/00*   (2006.01)
  *B82Y 15/00*  (2011.01)
  *A61F 2/848*      (2013.01)
  *A61F 2/82*       (2013.01)
  *B82Y 99/00*      (2011.01)

(52) U.S. Cl.
  CPC ............ *A61F 2210/0014* (2013.01); *A61F 2210/0076* (2013.01); *A61F 2250/0002* (2013.01); *A61F 2250/0043* (2013.01); *B82Y 15/00* (2013.01); *B82Y 99/00* (2013.01)

(56) References Cited

U.S. PATENT DOCUMENTS

| | | | |
|---|---|---|---|
| 5,807,258 | A | 9/1998 | Cimochowski |
| 6,840,956 | B1 | 1/2005 | Wolinksy |
| 7,340,288 | B1* | 3/2008 | Karicherla ............ A61B 5/0215 600/374 |
| 7,399,313 | B2 | 7/2008 | Brown |
| 2002/0026231 | A1* | 2/2002 | Shannon ................ A61F 2/07 623/1.13 |
| 2002/0183628 | A1* | 12/2002 | Reich ................ A61B 5/02014 600/486 |
| 2003/0032892 | A1* | 2/2003 | Erlach ................ A61B 5/0031 600/547 |
| 2004/0082867 | A1 | 4/2004 | Esch |
| 2005/0074479 | A1* | 4/2005 | Weber ................ A61F 2/0077 424/423 |
| 2006/0052865 | A1* | 3/2006 | Banas ................ A61F 2/07 623/1.44 |
| 2006/0129216 | A1* | 6/2006 | Hastings ................ A61B 5/445 607/115 |
| 2006/0136042 | A1* | 6/2006 | Holman ................ A61F 2/07 623/1.16 |
| 2007/0010868 | A1* | 1/2007 | Ferren ................ A61F 2/06 623/1.15 |
| 2007/0066929 | A1* | 3/2007 | Ferren ................ A61B 5/0002 604/8 |
| 2009/0036975 | A1* | 2/2009 | Ward ................ A61B 5/0031 623/1.18 |
| 2009/0132022 | A1* | 5/2009 | Banas ................ A61F 2/07 623/1.13 |
| 2010/0056985 | A1* | 3/2010 | Weber ................ A61B 1/00082 604/21 |
| 2012/0078999 | A1* | 3/2012 | Andrew ................ G06F 3/014 709/203 |
| 2016/0310026 | A1* | 10/2016 | Moen ................ A61B 5/02158 |
| 2019/0110747 | A1* | 4/2019 | Majerus ................ A61B 5/683 |

* cited by examiner

ACTIVE MONITORING PRESSURE SENSITIVE VASCULAR GRAFT

RELATED APPLICATIONS

The present application claims the benefit of U.S. Provisional Application No. 62/330,969, filed May 3, 2016, and U.S. Provisional Application No. 62/335,874, filed May 13, 2016, each of which is hereby incorporated herein by reference in its entirety.

TECHNICAL FIELD

Embodiments relate to vascular grafts, and in particular vascular grafts that can function as pressure-sensing endo-radiosondes.

BACKGROUND

To treat an abdominal aortic aneurysm, a transfemoral endovascular graft can be implanted to prevent further aneurismal growth or rupture. Once implanted, the graft provides a flowpath for blood to iliac and femoral arteries while protecting the wall of the artery from the high pressure it would otherwise be exposed to. This procedure, or some variation of it, has been available since at least the 1950s. See Santos et al., *Improving post-EVAR surveillance with a smart stent graft*, Technologies for medical sciences, Book Series: Lecture Notes in Computational Vision and Biomechanics, Chapter 14, vol. 1 (Natal Jorge, R. M.; Tavares, J. M. R. S.; Pinotti Barbosa, M.; Slade, A. P., Eds.) (2012). Modern abdominal aortic aneurysm treatment typically involves routing a catheter intra-arterially, from the femoral artery to the aneurysm location where the graft is deployed.

The aneurismal sac surrounding an installed endovascular graft can still be subject to rupture if blood is able to flow around or through the graft. The various failure modes can be caused by endoleaks. Known endoleaks can be classified into five types: (1) ineffective attachment or apposition to the vessel wall; (2) aneurismal sac filling through collateral branches; (3) a leak through a graft defect or junction of attachments between grafts; (4) leak through defective material making up the graft body; and (5) continued expansion of the aneurismal sac without appreciable angiographic feeders, commonly referred to as endotension.

Santos et al. describe three commercially available products that can be placed on or alongside a graft to measure the pressure of the blood within the aneurismal sac, and the relative benefits and detriments of each product.

First, Santos describes a system (the "Impressure AAA sac pressure transducer") that includes a piezoelectric membrane and a transducer. Upon activation of the transducer, the piezoelectric component can be used to sense a signal from an acoustic signal. The acoustic signal, therefore, must be applied directly to a portion of the patient where an ultrasonic signal can reach the graft. Because ultrasonic signal does not travel through bone or air, the Impressure AAA sac pressure transducer is cumbersome to use.

Second, Santos describes a system ("EndoSure wireless pressure sensor") that includes two conductive coils held in a pressure sensitive matrix. As the pressure changes in the aneurismal sac, the relative inductance and resonant frequency of these coils changes, and can be measured by a remote sensor. Although the EndoSure wireless pressure sensor does not require acoustic signal transmission to a detector, it does require specialized detection equipment and therefore would not typically be used continuously. Rather, the EndoSure wireless pressure sensor would typically only be used for occasional checkups. Furthermore, EndoSure can only measure absolute pressure, and not any particular portion in which pressure is higher or lower.

Third, Santos describes a system ("TPS telemetric pressure sensor") in which a capsule is installed adjacent to the graft. In the event that an endoleak or other failure occurs and pressure rises in the aneurismal sac, the capsule can detect that change in pressure and transmit an appropriate signal. Installation of a separate capsule increases complexity and requires suturing to the outer wall of the graft, potentially introducing failure sites.

It is desirable to provide a vascular graft that does not include or introduce additional failure modes or increase complexity of manufacturing. It is further desirable to provide a vascular graft that does not require use of ultrasound, has continuous monitoring capabilities, and can detect where the high pressure is located relative to the graft. Finally, it would be desirable to provide a system capable of identifying the reason why a failure has occurred, including the five types of known failure modes discussed above.

SUMMARY

Embodiments of the present application substantially address or meet the aforementioned needs of the industry. In embodiments, a graft having an inner wall and an outer wall each configured to sense deformation can be used to detect changes in pressure indicative of failures of the installed graft. Changes in vascular pressure along the inner wall relative to a baseline or control pressure can be indicative of leakage around the graft that reduces bloodflow through the graft. Likewise, changes in vascular pressure along the outer wall of the graft can be indicative of leakage at an aneurismal sac adjacent to the graft, in embodiments, or such changes in vascular pressure could be indicative of blood flow around the edge of the graft. Some types of leakage or misrouted blood flow can result in changes in vascular pressure on both the inner and outer walls of the graft, or changes in the peaks and/or troughs of that pressure as a function of time.

A vascular graft includes deformable sleeves that include an electrical component. The electrical component can be a variable-resistance or piezoelectric material, in embodiments, or other electric material such as one containing carbon nanotubes, silver nanoparticles, gold nanoparticles, or other biologically compatible materials for which deformation of the sleeves due to pressure changes create or modify an electrical signal. A transponder can then transmit information relating to the pressure inside and outside of the vascular graft.

The above summary is not intended to describe each illustrated embodiment or every implementation. The detailed description and claims that follow more particularly exemplify these embodiments.

BRIEF DESCRIPTION OF THE DRAWINGS

Embodiments may be more completely understood in consideration of the following detailed description of various embodiments of the invention in connection with the accompanying drawings, in which.

Figure 1:
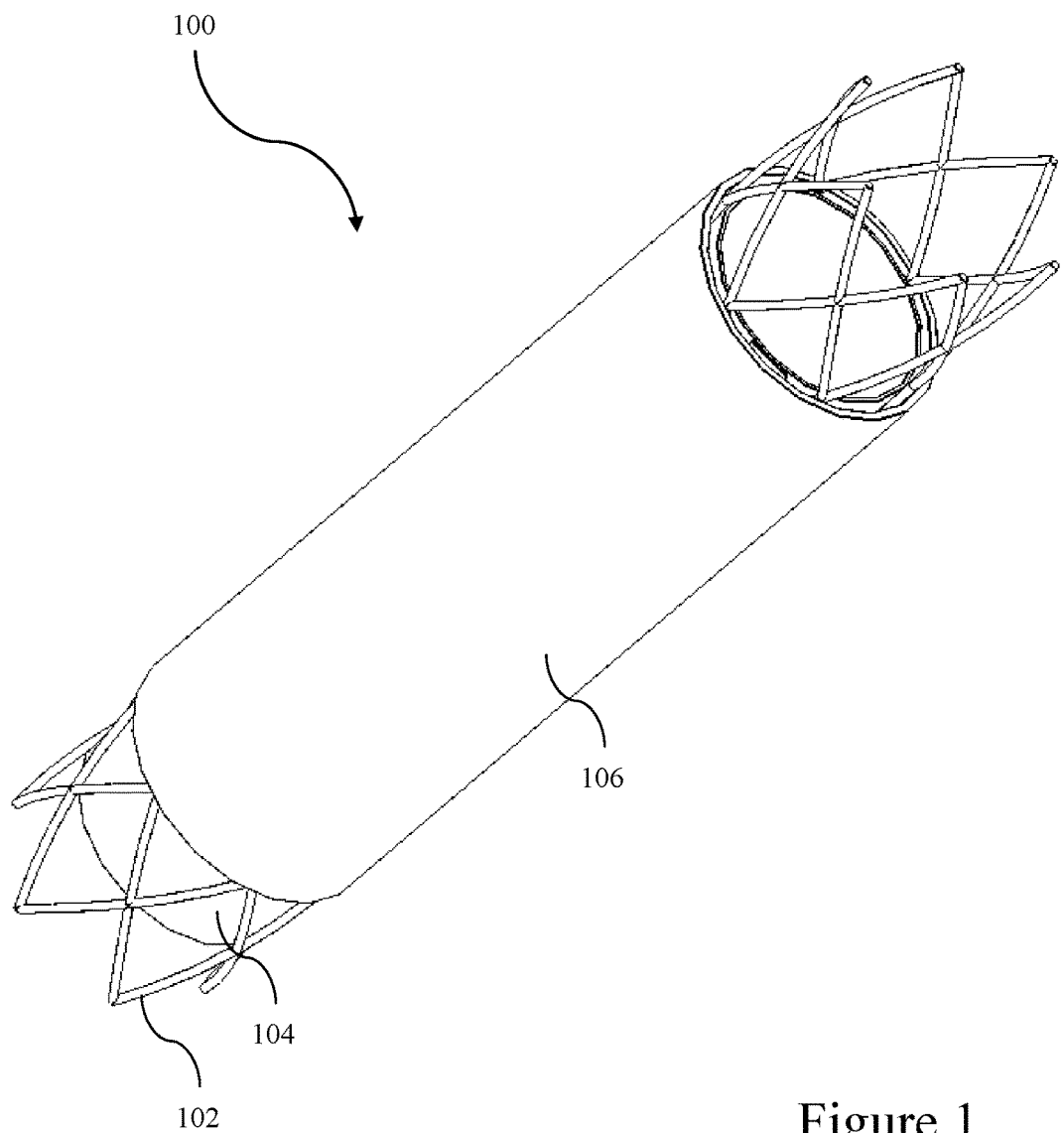
FIG. 1 is a perspective view of a vascular graft, according to an embodiment.

While embodiments are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Embodiments discussed herein incorporate pressure sensors into inner and outer walls of a vascular graft itself. During use, changes in pressure in the blood flowpath can be sensed by the inner wall of the vascular graft. Similarly, changes in pressure in the aneurismal sac can be sensed by the outer wall of the vascular graft. By employing an electrically responsive material, such as carbon nanotubes, material containing silver nanoparticles, or materials containing gold nanoparticles, a piezoelectric effect or a variable-resistance effect is created in the inner and outer walls of the vascular graft. Data corresponding to these effects can be sensed without the need for discrete focal sensors that can cause variations in graft profile. Furthermore, because such walls do not require suturing or otherwise attaching any sensors to the graft, there is no corresponding increase in the risk of failure modes in the graft itself.

The level of deformation of the walls is based on pressure against that wall. The pressure required to deform the wall can vary based upon the patient. For each patient, a baseline pressure results in no deformation of the walls. Therefore, absolute pressure can be measured and transmitted, rather than merely change in pressure. In some grafts, particularly larger grafts used in abdominal aortic aneurysm, the piezoelectric or variable-resistance materials can be incorporated into both inner and outer walls of the same graft. In those embodiments, it is possible to detect absolute pressure in the blood flowpath as well as the aneurismal sac.

Embodiments can be used in abdominal aortic aneurysm repair, thoracic aortic aneurysm repair, aortic ectasia, peripheral vascular atherosclerosis, visceral atherosclerosis, peripheral vascular aneurismal repair, and visceral aneurismal repair, for example. Other uses can include dialysis access, or arteriovenous dialysis grafts. In embodiments, systems described herein can be used for coronary bypass or other vascular bypass, such as visceral vascular bypass. Vascular conduits or shunts used in repair of congenital heart disease can also be included in embodiments.

FIG. 1 depicts an embodiment of a vascular graft 100. Vascular graft 100 includes a support lattice 102, an inner sleeve 104, and an outer sleeve 106. Vascular graft 100 can be positioned to route blood flow past an aneurysm or rupture, and to prevent further damage to the artery. In embodiments, vascular graft 100 can be routed intra-arterially to a desired position in a patient's vasculature.

Support lattice 102 is an interconnected network of a material such as a metal, a shape memory alloy, a shape memory polymer, or some other material that is deformable or flexible. In the embodiment shown in FIG. 1, support lattice 102 defines a generally cylindrical shape. In alternative embodiments, support lattice 102 can have any other shape, including bends, curves, apertures, or other features. Such features can be used to create a desired flow pattern through vascular graft 100. In embodiments, support lattice 102 can be collapsible, such that it expands as it is deployed from a device such as a catheter that routes vascular graft 100 to its desired location.

Inner sleeve 104 is radially inward from support lattice 102 in the embodiment shown in FIG. 1, and in use defines the outer wall of the flowpath through the artery. In order to maintain this flowpath, inner sleeve 104 can be impermeable to liquids. Inner sleeve 104 can detect the pressure against this wall and at the interface of the flowpath in embodiments, as described in more detail below with respect to FIGS. 5A-5D.

Outer sleeve 106, like inner sleeve 104, is arranged adjacent to support lattice 102. Outer sleeve 106 is arranged on the radially outer side of the cylindrical shape defined by support lattice 102. Furthermore, like inner sleeve 104, outer sleeve 106 can detect pressure against the outer wall.

In those embodiments in which support lattice 102 expands at delivery, inner sleeve 104 and outer sleeve 106 can be sufficiently elastic to stretch with the expansion of support lattice 102 during deployment. For example, inner sleeve 104 and outer sleeve 106 can include a polymeric material or film that is sufficiently elastic to expand with support lattice 102. Inner sleeve 104 and outer sleeve 106 can also include materials that change in resistance or generate electrical charge as they are deformed, as described in more detail with respect to FIGS. 5A-5D.

Figure 2:
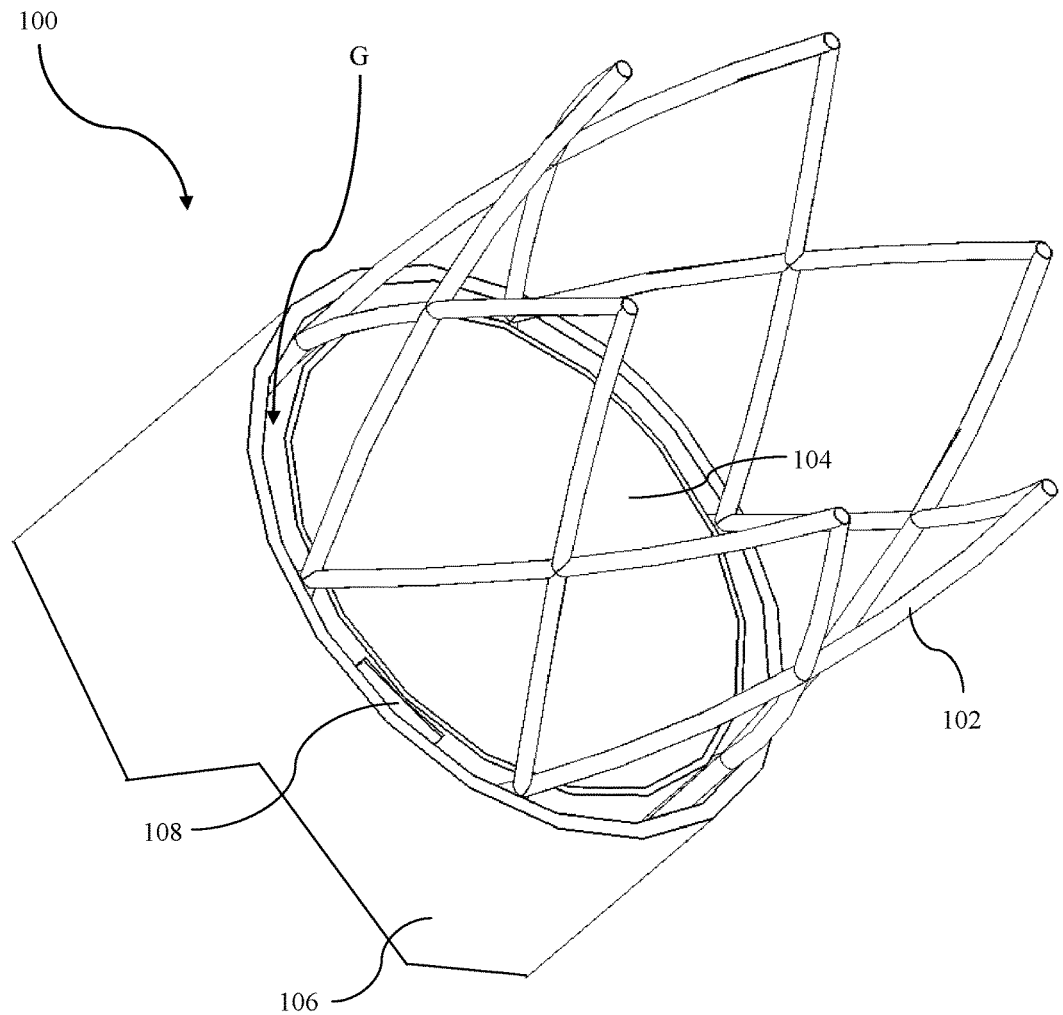
FIG. 2 is a cutaway perspective view of one end of the vascular graft of FIG. 1, depicting a transponder.

FIG. 2 is an enlarged, cutaway view of one end of vascular graft 100. In this enlarged view, transponder 108 is more clearly visible. Transponder 108 is a device that can communicate information related to a pressure. For example, in embodiments, transponder 108 is a radio frequency chip or some other type of transponder that can relay information regarding a pressure on inner sleeve 104 and/or a pressure on outer sleeve 106 to a remote reader. Transponder 108 is positioned in a gap G between inner sleeve 104 and outer sleeve 106. Support lattice 102 is also positioned in gap G.

Figure 3:
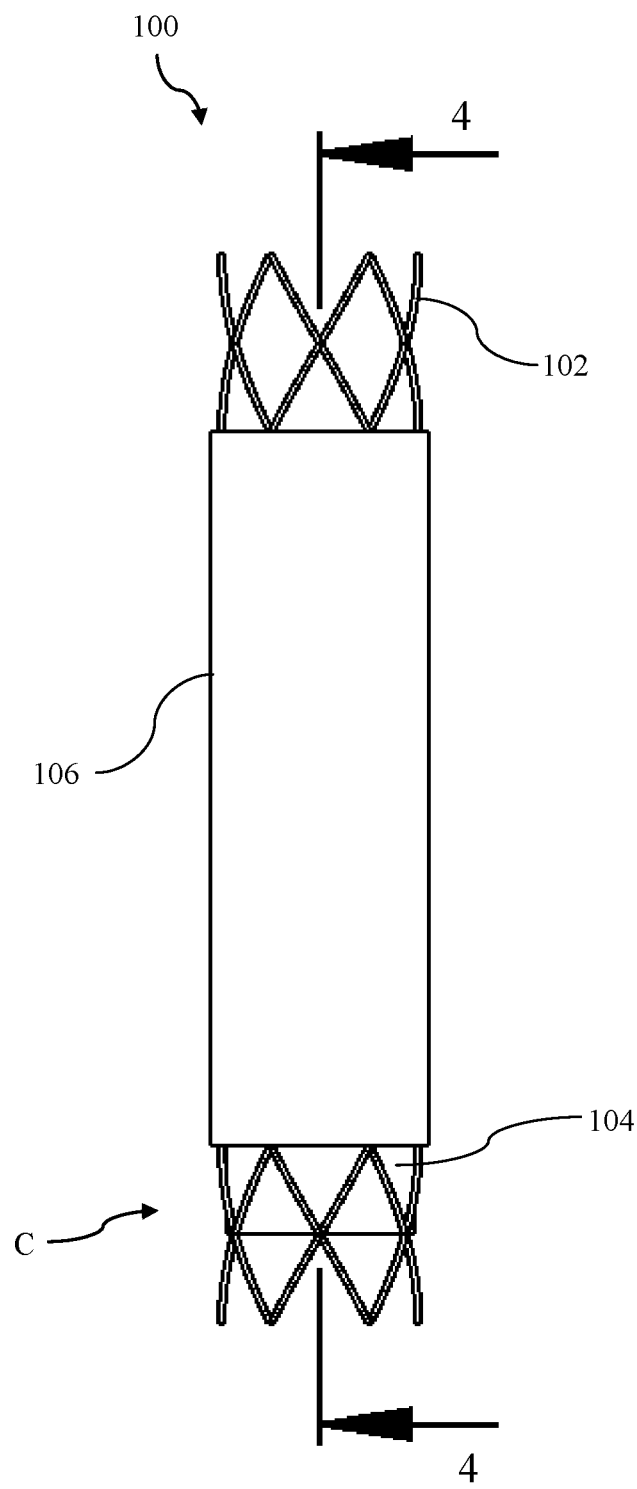
FIG. 3 is a side view of the vascular graft of FIGS. 1 and 2.

FIG. 3 is a side view of vascular graft 100, previously described with respect to FIGS. 1 and 2. FIG. 3 depicts inner sleeve 104 extending further parallel to line 4-4 than outer sleeve 106. In other embodiments, inner sleeve 104 and outer sleeve 106 can extend different amounts and may cover support lattice 102 in its entirety rather than leaving it exposed.

In embodiments, alternative vascular grafts can be configured to interconnect with other components by having inner or outer sleeves that extend different distances along their respective support lattices. For example, it may be desirable to connect two separate grafts together. To connect an adjoining vascular graft to graft 100 of FIG. 3, the adjoining graft can include a sleeve with a diameter approximately equal to that of outer sleeve 106. The sleeve of the adjoining graft can then be configured to slide over support lattice 102 and inner sleeve 104, forming a connection to vascular graft 100 at the connection portion C as shown in FIG. 3.

In alternative embodiments, other connections can be made between complimentary grafts. Complimentary grafts are those in which the longitudinal extent of the respective support lattices, inner sleeves, and outer sleeves can be engaged with one another to provide a flowpath through the two grafts. Complimentary grafts can be sealed to prevent flow from passing through or around the joint formed at their intersection. There is a possibility that a joint may not be properly sealed, however, or that the joint could degrade over time, causing leakage at or around the joint. Therefore, it can be desirable to have a mechanism for measuring pressure on both inside and outside of graft 100 such that leaks or other failures at the joint can be detected in those embodiments.

Figure 4:
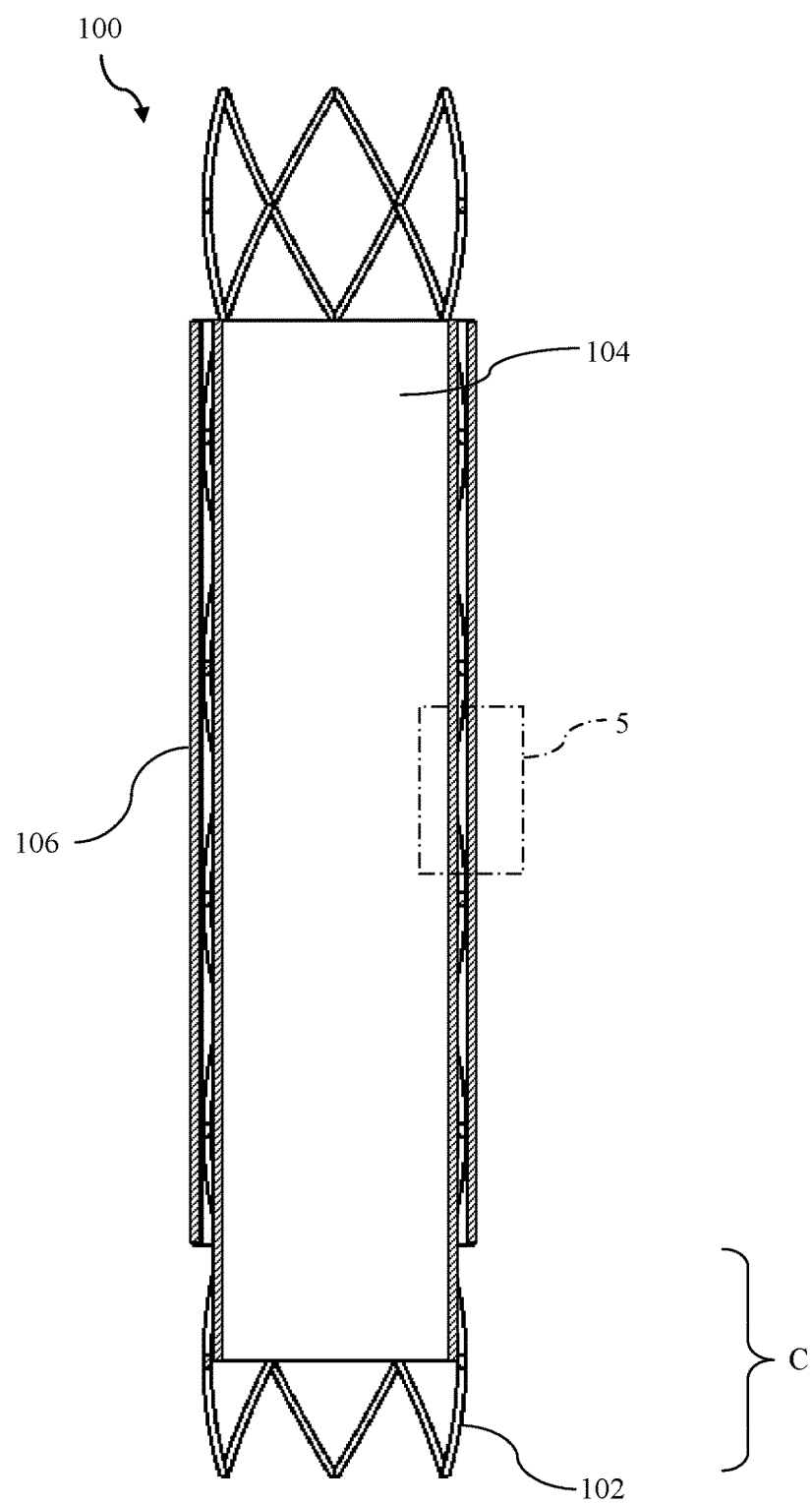
FIG. 4 is a cross-sectional view of the vascular graft of FIGS. 1-3, taken along cross-section 4-4 of FIG. 3.

FIG. 4 depicts vascular graft 100, shown in cross-section along line 4-4 of FIG. 3. As shown in FIG. 4, support lattice 102 extends between inner sleeve 104 and outer sleeve 106 along most of the length of graft 100. At connection portion C, support lattice 102 and inner sleeve 104 extend beyond the furthest longitudinal extent of outer sleeve 106. The boxed portion labeled "5" indicates a cutaway section be shown in more detail in FIGS. 5A-5D. Boxed portion 5 shows just one wall of graft 100, which includes both inner and outer layers and also includes a portion of support lattice 102.

FIGS. 5A-5D depict a partial cross-section of the section 5 depicted in FIG. 4. As shown in FIGS. 5A-5D, just one wall of vascular graft 100 is depicted. The wall shown in FIGS. 5A-5D includes both an inner sleeve 104 and an outer sleeve 106, which wrap around support lattice 102. As shown with respect to FIG. 4, the combined structure including the inner sleeve 104, outer sleeve 106, and support lattice 102 has a cylindrical superstructure to define a fluid conduit. In alternative embodiments, the wall formed of inner sleeve 104, outer sleeve 106, and support lattice 102 can form other shapes to form a plenum or conduit that is non-cylindrical.

In FIGS. 5A-5D, high pressure causes deformation at one or more of inner sleeve 104 or outer sleeve 106. Each sleeve (104, 106) includes several sub-components. In particular, inner sleeve 104 includes inner wall 1041, electrical component 104E, and outer wall 1040. Likewise, outer sleeve 106 includes inner wall 1061, electrical component 106E, and outer wall 1060. The terms "inner" and "outer," as used with respect to the walls (1041, 1040, 1061, 1060), refer to whether the walls are radially inner or outer with respect to the radial center of the vascular graft as previously depicted in FIGS. 1-4. The respective thicknesses of inner sleeve 104 and outer sleeve 106 are not necessarily to scale, nor are the relative thicknesses of the walls (1041, 1040, 1061, 1060) and electrical components (104E, 106E).

Inner walls 1041 and 1061, as well as outer walls 1040 and 1060, can be made of an insulating material. For example, walls 1041, 1061, 1040, and 1060 can include a polymeric material. In one embodiment, walls 1041, 1061, 1040, and 1060 can be polytetrafluoroethylene (PTFE) or Dacron. In other embodiments, walls 1041, 1061, 1040, and 1060 can be a biologic graft or material such as bovine grafts, cadaveric grafts, or cultured grafts. In some embodiments, such as those in which support lattice 102 expands at deployment from a catheter, it may be desirable for such polymeric material to also be elastic so that it is expansible with support lattice 102.

Electrical components 104E and 106E can be any of a number of materials configured to generate an electrical signal corresponding to a level of deformation of their respective sleeves 104, 106. In one embodiment, electrical components 104E and 106E can include a piezoelectric component configured to generate a charge when bent. In another embodiment, electrical components 104E and 106E could include a material having a variable resistance, such that a level of bending can be determined by sensing the resistance of the electrical components 104E and/or 106E. For example, electrical components 104E and 106E can be polytetrafluoroethylene (PTFE) or Dacron coated with or incorporating any suitable material, such as metallic nanoparticles or carbon nanotubes, that is biocompatible and exhibits an electrical effect under deformation. For example, in embodiments gold or silver nanoparticles, or carbon nanotubes, can be incorporated into electrical components 104E and/or 106E. Electrical components 104E and/or 106E including these materials can measure intraarterial pressure changes via deformation. In embodiments, electrical components 104E and 106E can include a gap or dielectric that separates electrically sensitive components on or between the inner and outer layers of each wall 104 and 106.

In embodiments, electrical components 104E and/or 106E need not fill the entirety of the gap G. Rather, electrical components 104E and/or 106E can comprise a coating of nanoparticles or nanotubes, for example, applied along either the inner wall (e.g., 1041 or 1061) or the outer wall (e.g., 1040 or 1060) of the sleeve.

As the electrical components 104E and/or 106E deform in shape their resistance changes, and the change of resistance provides a signal that can be calibrated to indicate pressure differentiations. Transponder 108 can receive a signal corresponding to this change in resistance and send out information from which intraarterial pressure and/or pressure outside vascular graft 100 can be determined.

Figure 5A:
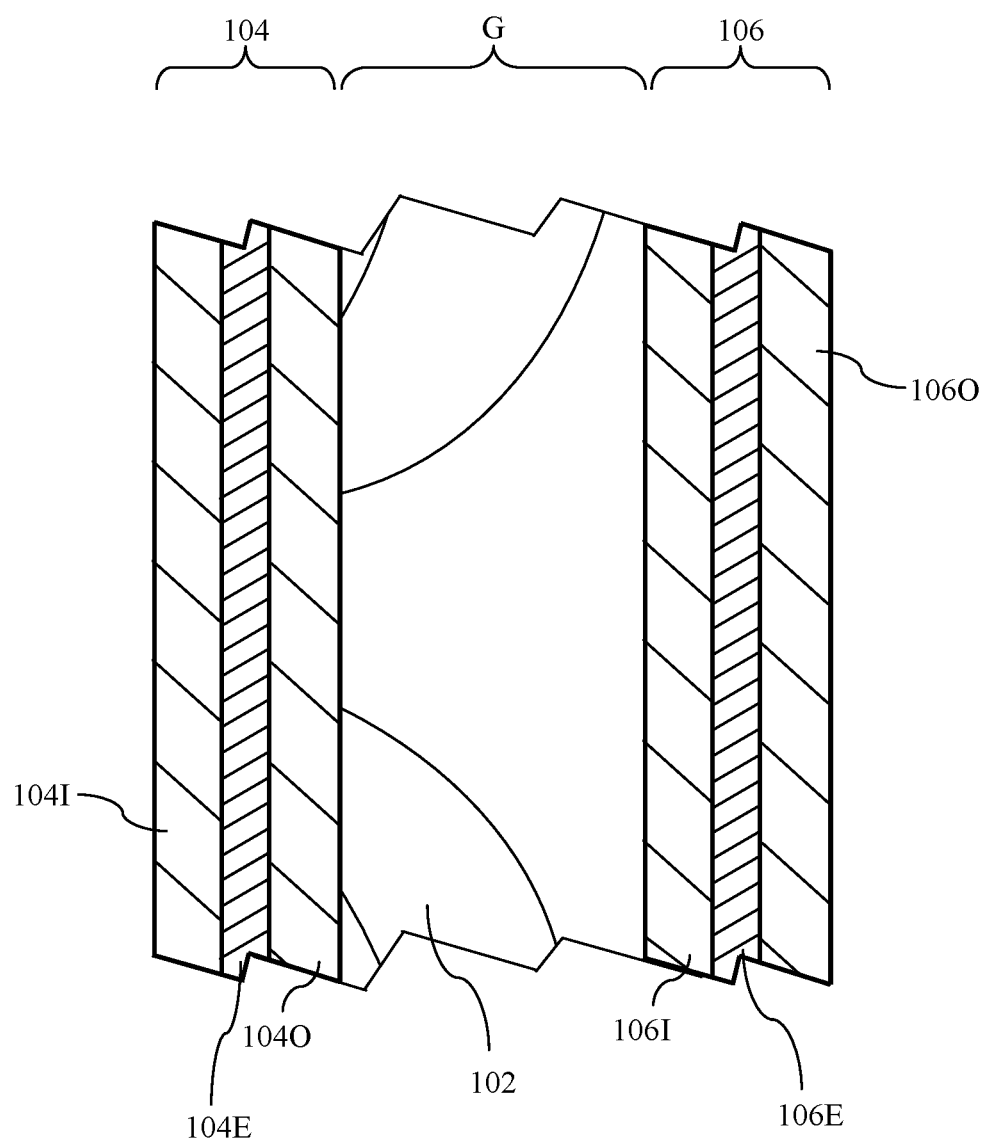
FIGS. 5A-5D depict the partial cross-section of box 5 shown in FIG. 4, according to one embodiment.
Figure 5B:
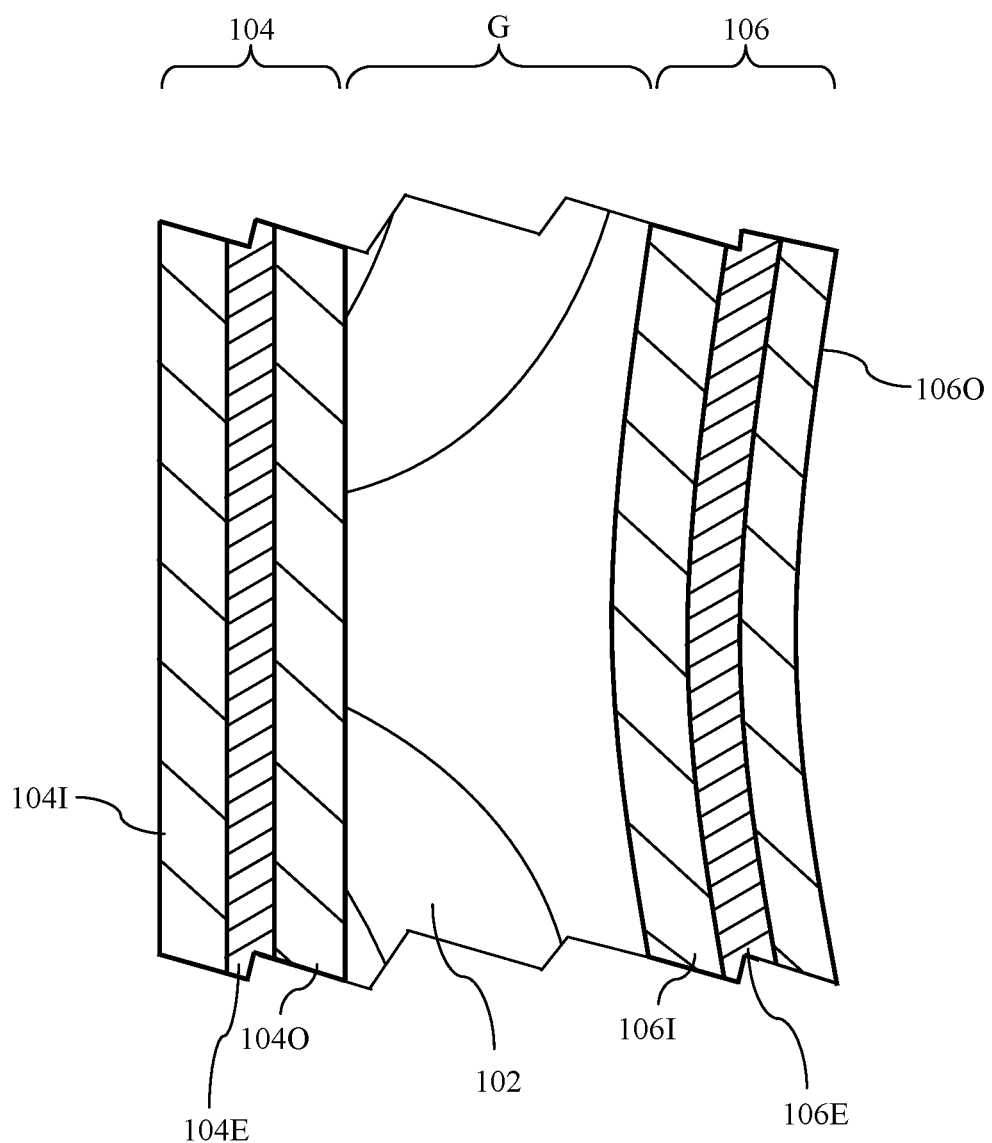
Figure 5C:
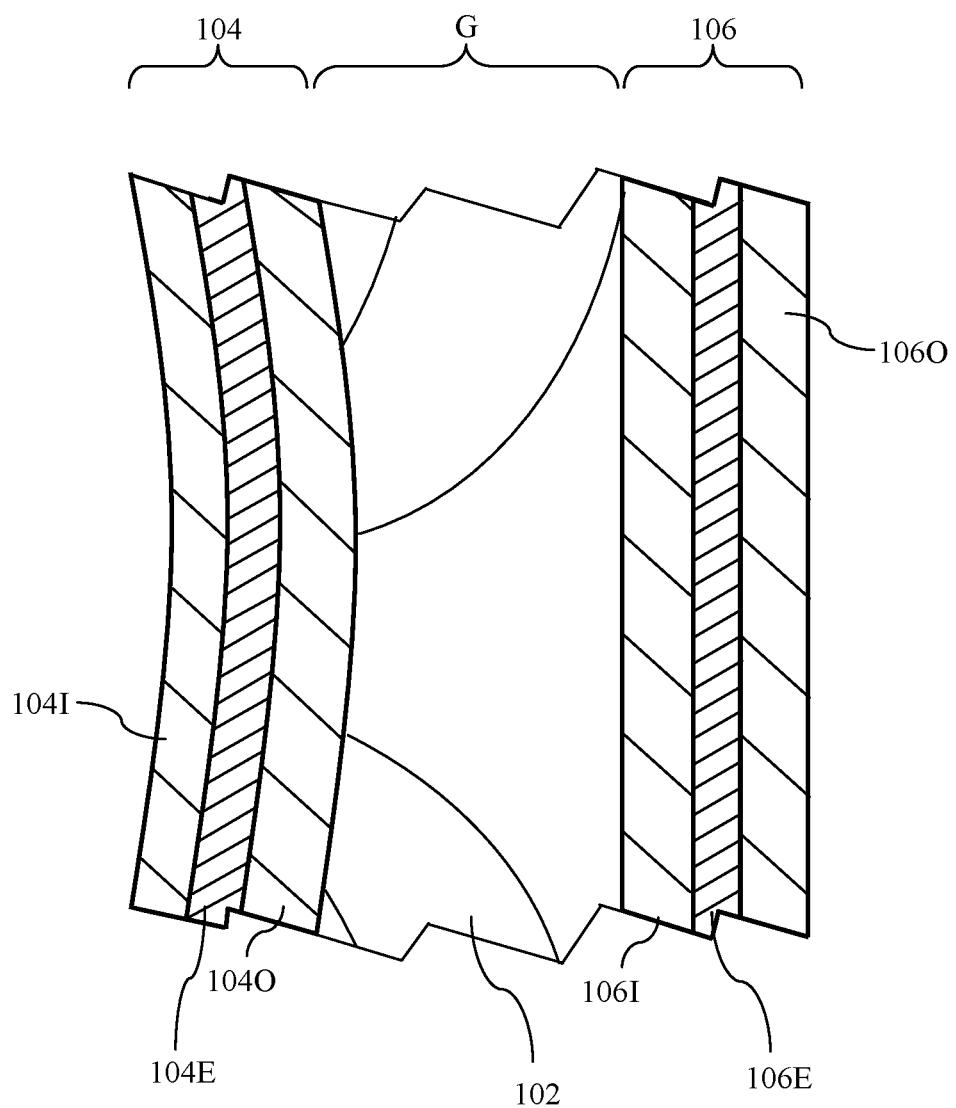
Figure 5D:
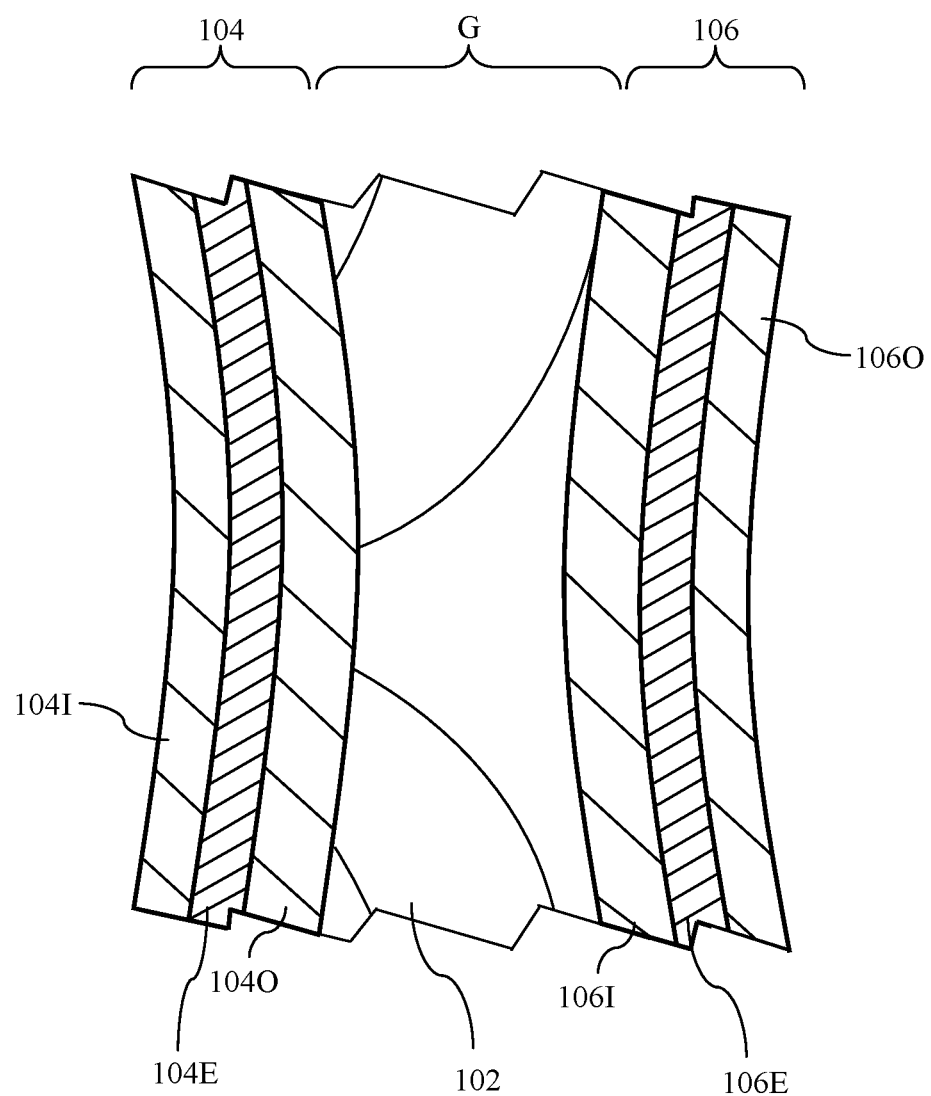

As shown in FIG. 5A, neither inner sleeve 104 nor outer sleeve 106 is deformed. In FIG. 5B, outer sleeve 1060 is deformed radially inwards, while inner sleeve 104 is not deformed. In FIG. 5C, inner sleeve 104 is deformed radially outwards, while outer sleeve 106 is not deformed. In FIG. 5D, both inner sleeve 104 and outer sleeve 106 are deformed.

Deformation of inner sleeve 104 can be measured and, in embodiment, compared with an expected or typical deformation waveform. Some deformation of inner sleeve 104 is expected during systole as the pressure of the blood flow through graft 100 increases. Irregular patterns, an increase in deformation, or a decrease in deformation all can be indicators of various cardiac disorders or failures of graft 100.

Deformation of outer sleeve 106 can also provide information regarding the operation of graft 100. In particular, deformation of outer sleeve 106 can indicate that the aneurismal sac is leaking. In some circumstances, by comparing the wave form of the pressure (and accompanying deformation of sleeve 106) to the wave form at inner sleeve 104, it is possible to ascertain the type of failure that has caused the aneurismal sac to fill.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112(f) of 35 U.S.C. are not to be invoked unless the specific terms "means for" or "step for" are recited in a claim.

The invention claimed is:

1. A vascular graft comprising:
    a support lattice defining an enclosed flowpath;
    an inner sleeve disposed along a radially inner portion of the support lattice, the inner sleeve comprising a deformable material and a first electrical component coupled to the deformable material, the first electrical component at least partially spanning along the inner sleeve in a continuous first layer, the first electrical component configured to produce an electrical signal indicative of a level of deformation;
    an outer sleeve disposed along a radially outer portion of the support lattice, the outer sleeve comprising a deformable material and a second electrical component coupled to the deformable material, the second electrical at least partially spanning along the outer sleeve in a continuous second layer, the second electrical component configured to produce an electrical signal indicative of a level of deformation; and
    a transponder electronically coupled to the inner sleeve and the outer sleeve and configured to transmit a signal corresponding to the level of deformation of the inner sleeve and the level of deformation of the outer sleeve.

2. The vascular graft of claim 1, wherein the inner sleeve comprises:
    an inner wall,
    an outer wall, and
    the first electrical component arranged between the inner wall and the outer wall, wherein the first electrical component is configured to produce the electrical signal indicative of the level of deformation.

3. The vascular graft of claim 2, wherein the inner wall and the outer wall each comprise a liquid impermeable membrane.

4. The vascular graft of claim 2, wherein the inner wall and the outer wall are selected from the group consisting of:
    polytetrafluoroethylene (PTFE);
    polyethylene terephthalate; and
    a biologic graft.

5. The vascular graft of claim 2, wherein the first electrical component comprises a coating of metallic nanoparticles arranged between the inner wall and the outer wall.

6. The vascular graft of claim 2, wherein the first electrical component comprises carbon nanotubes.

7. The vascular graft of claim 1, wherein the outer sleeve comprises:
    an inner wall,
    an outer wall, and
    the second electrical component arranged between the inner wall and the outer wall, wherein the second electrical component is configured to produce the electrical signal indicative of the level of deformation.

8. The vascular graft of claim 7, wherein the second electrical component comprises a coating of metallic nanoparticles arranged between the inner wall and the outer wall.

9. The vascular graft of claim 7, wherein the second electrical component comprises carbon nanotubes.

10. The vascular graft of claim 1, wherein the support lattice comprises an interconnected network of a lattice material.

11. The vascular graft of claim 1, wherein the lattice material comprises a shape memory alloy.

12. The vascular graft of claim 1, wherein the enclosed flowpath defines a longitudinal flow direction, and wherein the support lattice and the inner sleeve extend beyond the furthest longitudinal extent of the outer sleeve.

* * * * *